United States Patent
Vonderhagen (12)

(10) Patent No.: US 6,479,618 B1
(45) Date of Patent: Nov. 12, 2002

(54) ENZYMATIC ESTERIFICATION

(75) Inventor: Anja Vonderhagen, Duesseldorf (DE)

(73) Assignee: Cognis Deutschland GmbH, Duesseldorf (DE)

(*) Notice: Subject to any disclaimer, the term of this patent is extended or adjusted under 35 U.S.C. 154(b) by 0 days.

(21) Appl. No.: 09/857,633

(22) PCT Filed: Dec. 1, 1999

(86) PCT No.: PCT/EP99/09378

§ 371 (c)(1),
(2), (4) Date: Jun. 7, 2001

(87) PCT Pub. No.: WO00/34501

PCT Pub. Date: Jun. 15, 2000

(30) Foreign Application Priority Data

Dec. 10, 1998 (DE) .......................... 198 56 948

(51) Int. Cl.$^7$ .............................. C08G 63/78
(52) U.S. Cl. .................. 528/274; 528/301; 528/302; 528/306; 528/308; 528/308.6; 524/765; 435/183
(58) Field of Search ................ 528/274, 301, 528/302, 306, 308, 308.6; 524/765; 435/183; 424/94.6

(56) References Cited

U.S. PATENT DOCUMENTS

| | | | |
|---|---|---|---|
| 4,172,887 A | 10/1979 | Vanlerberghe et al. |
| 4,853,430 A | 8/1989 | Stuehler et al. |
| 5,147,791 A | 9/1992 | Morrow et al. |
| 5,478,910 A | 12/1995 | Russell et al. |
| 5,705,169 A | 1/1998 | Stein et al. |
| 5,730,960 A | 3/1998 | Stein et al. |
| 5,807,540 A | 9/1998 | Junino et al. |
| 5,962,624 A | 10/1999 | Vonderhagen et al. |
| 6,193,960 B1 | 2/2001 | Metzger et al. |

FOREIGN PATENT DOCUMENTS

| | | |
|---|---|---|
| CA | 2071365 | 12/1992 |
| DE | 1 165 574 | 3/1964 |
| DE | 20 24 051 C3 | 10/1979 |
| DE | 197 53 789 A1 | 6/1999 |
| EP | 0 229 400 A3 | 7/1987 |
| EP | 0 383 405 A1 | 8/1990 |
| EP | 0 519 727 A1 | 12/1992 |
| EP | 0 693 471 A1 | 1/1996 |
| EP | 0 694 521 A1 | 1/1996 |
| EP | 0 740 933 A1 | 11/1996 |
| EP | 0 818 450 A1 | 1/1998 |
| FR | 2 252 840 A | 8/1975 |
| GB | 962919 | 7/1964 |
| GB | 1 333 475 | 10/1973 |
| GB | 2 272 904 A | 6/1994 |
| WO | WO94/12652 | 6/1994 |
| WO | WO98/55642 | 12/1998 |
| WO | WO99/46397 | 9/1999 |

OTHER PUBLICATIONS

Uyama, et al., "Enzymatic Polymerization of Dicarboxylic Acid and Glycol to Polyester in Solvent–Free System", Chemistry Letters, vol. 12, Dec. 1998, pp. 1285–1286, XP002134708 The Chemical Society of Japan.

Kline, et al., "Synthesis and Characterization of Aliphatic Polyesters with Hydrophilic Pendant Groups Using Enzymes", Chemical Abstracts + Indexes, US, American Chemical Society, Columbus, vol. 20, No. 129, Nov. 16, 1998, XP002106733, ISSN: 0009–2258.

Kobayashi, et al., Dehydration Polymerization in Aqueous Medium Catalyzed by Lipase, Chemistry Letters, vol. 11, Nov. 1997, p. 105 XP002134709 The Chemical Society of Japan, JP.

Berkane, et al., "Lipase–Catalyzed Polyester Synthesis in Organic Medium. Study of Ring–Chain Equilibrium" Macromolecules, US, American Chemical Society, Easton, vol. 30, No. 25, Dec. 15, 1997, pp. 7729–7734, XP000727536, ISSN: 0024–9297.

Todd, et al., "Volatile Silicone Fluids for Cosmetic Formulations", Cosmetics & Toiletries, vol. 91, (Jan., 1976), pp. 29–32.

Tronnier, et al., "Experimentelle Untersuchungen zur Wirkungsweise Aluminiumhaltiger Antiperspiranzien", J. Soc. Cosmetic Chemists, vol. 24, (1973), pp. 281–290.

Graham, et al., "Inhibition of the Mitochondrial Oxidation of Octanoate by Salicyclic Acid and Related Compounds", J. Pharm. Pharmac., vol. 26, (1974), pp. 531–534.

Lochhead, et al., "Encyclopedia of Polymers and Thickeners for Cosmetics", Cosmetics & Toiletries, vol. 108, Allured Publishing Corp., (May, 1993), pp. 95–135.

Finkel, "Formulierung Kosmetischer Sonnenschutzmittel", SOFW–Journal, vol. 122, (1996), pp. 543–548.

"Kosmetische Färbemittel", Farbstoffkommission der Deutschen Forschungsgemeinschaft, Verlag Chemie, Weinheim, (1984), pp. 81–106.

Primary Examiner—Samuel A. Acquah
(74) Attorney, Agent, or Firm—John E. Drach; Aaron R. Ettelman

(57) ABSTRACT

Processes for preparing linear polyesters by reacting a dicarboxylic acid having from 2 to 10 carbon atoms, a polyol having from 2 to 15 carbon atoms, a low-boiling primary alcohol and a catalytic-effective amount of a lipase, wherein the reaction mixture is free of additional solvents; are described. The use of such linear polyesters in cosmetics is also described.

18 Claims, No Drawings

ENZYMATIC ESTERIFICATION

BACKGROUND OF THE INVENTION

Chemically, the esterification of dicarboxylic acids with polyhydric alcohols is very difficult to control and gives highly crosslinked polyesters at very high temperatures, i.e. beyond the melting points of the dicarboxylic acids. By contrast, the lipase-catalyzed transesterification of dicarboxylic acid esters leads to the formation of linear polyesters under mild reaction conditions. By contrast, the esterification of the free dicarboxylic acids depends on the use of a solvent because the optimal reaction temperatures of the lipase are below the melting temperatures of the dicarboxylic acids.

Since the free dicarboxylic acids are more readily accessible on an industrial scale than their esters, the problem addressed by the present invention was to provide a new process which would enable linear polyesters to be obtained in quantitative yields and favorable reaction times from dicarboxylic acids and polyols under mild conditions without the use of solvents.

BRIEF SUMMARY OF THE INVENTION

The present invention relates, in general, to processes for the production of linear polyesters from aliphatic, substituted aliphatic, aromatic and/or substituted aromatic dicarvoxylic acids and polyols in the presence of small quantities of a low-boiling primary alcohol and lipase as catalyst but without the addition of solvent. The linear polyesters can be used as thickeners and softeners in cosmetic preparations.

The present invention also relates to the use of linear polyesters obtained by reaction of aliphatic, substituted aliphatic, aromatic and/or substituted aromatic dicarboxylic acids containing 2 to 10 carbon atoms and polyols containing 2 to 15 carbon atoms and at least two primary hydroxyl groups in the presence of small quantities of a low-boiling primary alcohol and lipase as catalyst without the addition of solvents as thickeners and softeners in cosmetic preparations.

It has surprisingly been found that linear polyesters can be obtained from dicarboxylic acids and polyols for the first time without the addition of solvents providing the reaction is carried out in the presence of a low-boiling primary alcohol and lipase as catalyst. The esterification is distinguished by mild reaction conditions, favorable reaction times and quantitative yields. The invention includes the observation that advantageously water-soluble linear polyesters are also obtained where dicarboxylic acid mixtures containing hydroxydicarboxylic acids are used.

DETAILED DESCRIPTION OF THE INVENTION

Dicarboxylic Acids

Aliphatic, substituted aliphatic, aromatic and/or substituted aromatic dicarboxylic acids containing 2 to 10, preferably 3 to 9 and more preferably 4 to 6 carbon atoms are used for the production of polyesters. The aliphatic dicarboxylic acids used include, for example, oxalic acid, malonic acid, succinic acid and adipic acid, azelaic acid, dodecanedioic acid and brassylic acid while the aromatic dicarboxylic acids used include phthalic acid, isopthalic acid and terephthalic acid. The substituted dicarboxylic acids used include the aminodiacids, preferably glutamic acid, and hydroxydicarboxylic acids containing at least two primary hydroxyl groups, preferably maleic acid, citric acid, glutaconic acid and glutaric acid and, more particularly, tartaric acid. Aliphatic unbranched dicarboxylic acids and hydroxydicarboxylic acids are preferably used.

In addition, mixtures of dicarboxylic acids may be used, in which case at least one dicarboxylic acid is a hydroxydicarboxylic acid containing at least two primary hydroxyl groups, preferably malic acid, citric acid, glutaconic acid and glutaric acid and, more particularly, tartaric acid. The molar ratio of dicarboxylic acid to hydroxydicarboxylic acid is 1:10 to 10:1, preferably 1:5 to 5:1 and more preferably 1:2 to 1:1.

Polyols

Polyols suitable for the purposes of the invention preferably contain 2 to 15, more preferably 3 to 7 and more particularly 4 to 6 carbon atoms and at least 2, preferably at most 6 and more particularly 3 hydroxyl groups. The polyols may contain other functional groups, more particularly amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preferred alkylene glycols are propylene glycol, butylene glycol, hexylene glycol and polyethylene glycols with an average molecular weight of 100 to 1,000 dalton. Particularly suitable polyols are glycerol, sorbitol, sorbitan, trimethylol propane, pentaerythritol and 2-aminopropane-1,3-diol. Oligomers thereof, for example dimers, trimers, tetramers, pentamers and/or hexamers, may also be used.

Low-boiling Primary Alcohols

Low-boiling primary alcohols suitable for the purposes of the invention are alcohols with a boiling point below 100° C. Methanol, isopropanol and propanol and particularly ethanol are preferably used.

Lipases

Lipases derived from *Candida cylindracea, Candida lipolytica, Candida rugosa, Candida antarctica* B, *Candida utilis, Chromobacterium viscosum, Geotrichum viscosum, Geotrichum candidum, Mucor javanicus, Mucor miehei, porcine pancreas*, Pseudomonas species, *Pseudomonas* fluorescens, Pseudomonas sepacia, Rhizomucor miehei, Rhizopus arrhizus, Rhizopus delemar, Rhizopus delemar, Rhizopus niveus, Rhizopus oryzae, Aspergillus niger, Penicillium roquefortii, Penicillum cambertii, Pseudomonas fluorescens or from an esterase of Bacillus sp., Bacillus thermoglucosidasius, Mucor miehei, horse liver, Saccharomyces cerevisiae, pig liver are used as catalyst for the production of the linear polyols according to the invention. The lipases may be used individually or in combination with one another. The lipases are used in quantities which effect adequate catalysis of the polyesterification according to the invention and lead to a desired molecular weight of the linear polyesters. Lipases derived from Mucor miehei and Aspergillus niger are preferably used. In particular, Novozym® 388 L (Rhizomucor miehei lipase, free), Lipozym® IM (Rhizomucor miehei lipase, immobilized), Novozym® 735 L (Candida antarctica B lipase, free), Novozym® 525 L (Candida antarctica B lipase, free) and/or Novozym® 435 (Candida antarctica B lipase, immobilized), which are all products of Nono Nordisk, Denmark, are used. The lipases are preferably used in quantities of 0.01 to 15% by weight and more particularly in quantities of 1 to 10% by weight, based on the dicarboxylic acid.

Production Process

According to the invention, the linear polyols are obtained by reaction of mixtures of dicarboxylic acids containing a hydroxydicarboxylic acid with polyols in the presence of small quantities of a low-boiling primary alcohol and lipase as catalyst without the addition of solvents. The low-boiling alcohol released is preferably removed from the reaction mixture. The reaction is carried out at temperatures of preferably 50 to 90° C. and more particularly 70° C. and under pressures of generally 0 to 1013, preferably 0.01 to 500 and more preferably 10 to 250 mbar. The reaction time is 8 hours to 4 days and preferably 24 to 48 hours. To produce the polyesters according to the invention, the dicarboxylic acids and polyols are used in a molar ratio of 2:1 to 0.5:1 and preferably 1.2:1 to 0.8:1. The low-boiling primary alcohols are used in a 0.1 to 5 molar, preferably 0.2 to 2 molar and more preferably 0.3 to 1 molar excess, based on the dicarboxylic acid. Polyesters with a molecular weight of 483 to 10,000 (as determined from GPC data and calibration with polyethylene glycol) or 22,000 (as determined from GPC data and calibration with polystyrene) may be obtained by this process.

Commercial Applications

The linear polyesters according to the invention may be used for the production of cosmetic preparations such as, for example, hair shampoos, hair lotions, foam baths, shower baths, creams, gels, lotions, alcoholic and aqueous/alcoholic solutions, emulsions, oils, wax/fat compositions, stick preparations, powders or emollients. These preparations may contain mild surfactants, oil components, emulsifiers, superfatting agents, pearlizing waxes, consistency factors, thickeners, polymers, silicone compounds, fats, waxes, stabilizers, biogenic agents, deodorizing agents, antidandruff agents, film-formers, swelling agents, UV protection fractors, antioxidants, hydrotropes, preservatives, insect repellents, self-tanning agents, solubilizers, perfume oils, dyes, germ inhibitors and the like as further auxiliaries and additives.

Typical examples of suitable mild, i.e. dermatologically compatible, surfactants are fatty alcohol polyglycol ether sulfates, monoglyceride sulfates, mono- and/or dialkylsulfosuccinates, fatty acid isethionates, fatty acid sarcosinates, fatty acid taurides, fatty acid glutamates, ether carboxylic acids, alkyl oligoglucosides, fatty acid glucamides, alkyl amidobetaines and/or protein fatty acid condensates (preferably based on wheat proteins).

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of hydroxycarboxylic acids with linear or branched $C_{6-22}$ fatty alcohols, more particularly dioctyl malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons.

Suitable emulsifiers are, for example, nonionic surfactants from at least one of the following groups:

(1) products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group;

(2) $C_{12/18}$ fatty acid monoesters and diesters of addition products of 1 to 30 moles of ethylene oxide onto glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) products of the addition of 15 to 60 moles of ethylene oxide onto castor oil and/or hydrogenated castor oil;

(6) polyol esters and, in particular, polyglycerol esters such as, for example, polyglycerol polyricinoleate, polyglycerol poly-12-hydroxysterate or polyglyerol dimerate isostearate. Mixtures of compounds from several of these classes are also suitable;

(7) products of the addition of 2 to 15 moles of ethylene oxide onto castor oil and/or hydrogenated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) mono-, di- and trialkyl phosphates and mono-, di- and/or tri-PEG-alkyl phosphates and salts thereof;

(10) wool wax alcohols;

(11) polysiloxane/polyalkyl polyether copolymers and corresponding derivatives;

(12) mixed esters of pentaerythritol, fatty acids, citric acid and fatty alcohol according to DE 11 65 574 PS and/or mixed esters of fatty acids containing 6 to 22 carbon atoms, methyl glucose and polyols, preferably glycerol or polyglycerol;

(13) polyalkylene glycols and

(14) glycerol carbonate.

Products of the addition of ethylene oxide and/or propylene oxide onto fatty alcohols, fatty acids, alkylphenols, glycerol monoesters and diesters and sorbitan monoesters and diesters of fatty acids or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as refatting agents for cosmetic compositions from DE 20 24 051 PS.

$C_{8/18}$ alkyl mono- and oligoglycosides, their production and their use are known from the prior art. They are produced in particular by reacting glucose or oligosaccharides with primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH—or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers may also be used, those of the esterquat type, preferably methyl-quaternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400°, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryidimonium Hydroxypropyl Hydrolyzed Collagen (Lamequat® L, Grünau GmbH), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz AG), copolymers of acrylic acid with dimethyl diallyl ammonium chloride (Merquat® 550, Chemviron), polyaminopolyamides as described, for example, in FR 2 252 840 A and crosslinked water-soluble polymers thereof, cationic chitin derivatives such as, for example, quatemized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar®C-17, Jaguar®C-16 of Celanese, USA, quaternized ammonium salt polymers such as, for example, Mirapol® A-15, Mirapol® AD-1, Mirapol® AZ-1 of Miranol, USA.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. In addition, a detailed review of suitable liquid silicones was published by Todd et al. in Cosm. Toil. 91, 27 (1976).

Typical examples of fats are glycerides while suitable waxes are inter alia beeswax, carnauba wax, candelilla wax, montan wax, paraffin wax, hydrogenated castor oils, fatty acid esters solid at room temperature or microwaxes, optionally in combination with hydrophilic waxes, for example cetyl stearyl alcohol or partial glycerides. Metal salts of fatty acids such as, for example, magnesium, aluminum and/or zinc stearate or ricinoleate, may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Suitable deodorizers are, for example, antiperspirants, such as aluminum chlorhydrates. These antiperspirants are colorless hygroscopic crystals which readily deliquesce in air and which accumulate when aqueous aluminum chloride solutions are concentrated by evaporation. Aluminum chlorhydrate is used for the production of perspiration-inhibiting and deodorizing compositions and probably acts by partially blocking the sweat glands through the precipitation of proteins and/or polysaccharides [cf. J. Soc. Cosm. Chem. 24, 281 (1973)]. For example, an aluminum chlorhydrate which corresponds to the formula $[Al_2(OH)_5Cl].2.5H_2O$ and which is particularly preferred for the purposes of the invention is commercially available under the name of Locron® from Hoechst AG of Frankfurt, FRG [cf. J. Pharm. Pharmcol. 26, 531 (1975)]. Besides the chlorhydrates, aluminum hydroxylactates and acidic aluminum/zirconium salts may also be used. Other suitable deodorizers are esterase inhibitors, preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in stick products. Examples of such antibacterial agents are chitosan, phenoxyethanol and chlorhexidine gluconate. 5-Chloro-2-(2,4-dichloro-phenoxy)-phenol, which is marketed under the name of Irgasan® by CibaGeigy of Basel, Switzerland, has also proved to be particularly effective.

Suitable antidandruff agents are climbazol, octopirox and zinc pyrithione. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Examples of UV protection factors include organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor, as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxy-benzophenone, 2-hydroxy-4-methoxy-4'-methylbenzophenone, 2,2' -dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone, as described in EP0 818 450 A1;

propane-1,3-diones such as, for example, 1-(4-tert.butylphenyl)-3-(4'-methoxyphenyl)-propane-1,3-dione;

ketotricyclo(5.2.1)decane derivatives, as described in EP 0 694 521 B1.

Suitable water-soluble substances are 2-phenylbenzimidazole-5-sulfonic acid and alkali metal, alkaline earth metal, ammonium, alkylammonium, alkanolammonium and glucam-monium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example I-(4'-tert.butylphenyl)-3-(4'-methoxyphenyl)-propane-1,3-dione, 4-tert-butyl4'-methoxydibenzoylmethane (Parsol 1789) or 1-phenyl-3-(4'-isopropylphenyl)-propane-1,3-dione. The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminum and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have an average diameter of less than 100 nm, preferably from 5 to 50 nm and more preferably from 15 to 30 nm. They may be spherical in shape although ellipsoidal particles or other non-spherical particles may also be used. So-called micro- or nanopigments are preferably used in sun protection products. Micronized zinc oxide is preferably used.

Other suitable UV filters can be found in P. Finkel's review in SÖFW-Journal 122, 543 (1996).

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-camosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, λ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example $ZnO$, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. These dyes are normally used in concentrations of 0.001 to 0.1% by weight, based on the mixture as a whole.

Typical examples of germ inhibitors are preservatives which act specifically against gram-positive bacteria such as, for example, 2,4,4'-trichloro-2'-hydroxydiphenyl ether, chlorhexidine (1,6-di-(4-chlorophenyl-biguanido)-hexane) or TCC (3,4,4'-trichlorocarbanilide). Numerous perfumes and essential oils also have antimicrobial properties. Typical examples are the active substances eugenol, menthol and thymol in clove, mint and thyme oil. An interesting natural deodorant is the terpene alcohol farnesol (3,7,11-trimethyl-2,6,10-dodecatrien-1-ol) which is present in linden blossom oil and which smells of lily-of-the-valley. Glycerol monolaurate has also been successfully used as a bacteriostatic agent. The percentage content of the additional germ-inhibiting agents is normally about 0.1 to 2% by weight, based on the solids component of the preparations.

The total percentage content of auxiliaries and additives may be from 1 to 50% by weight and is preferably from 5 to 40% by weight, based on the particular composition. The compositions may be produced by standard hot or cold processes and are preferably produced by the phase inversion temperature method.

EXAMPLES

Example 1

4.6 g of ethanol (0.1 mole) and 9.2 g (0.1 mole) of glycerol were added to 18.2 g (0.1 mole) of azelaic acid and the reaction was started with 1.4 g (5% by weight) of Novozym® 435 (immobilized *Candida antarctica* B lipase from Novo Nordisk). After the reaction mixture had been stirred for 4 hours at 75° C./1013 mbar, the pressure was reduced to 500 mbar and later to 50 mbar to continuously distill off the ethanol. After 24 hours, the immobilized enzyme was removed by filtration. A yellow viscous liquid with a molecular weight (as determined from GPC data and calibration with polystyrene) of ca. 1200 and an acid value of ca. 50 was obtained in a yield of about 25 g.

Examples 2 and 3

The same reaction as in Example 1 was carried out with 6.0 g (0.1 mol) of isopropanol or propanol instead of ethanol, comparable results being obtained.

Example 4

46.1 g (1 mole) of ethanol and 184.2 g (1 mole) of glycerol were added to 150.1 g (1 mole) of L-(+)-tartaric acid and 188.2 g (1 mole) of azelaic acid and the reaction was started with 26 g (5% by weight) of Novozym® 435 (immobilized *Candida antarctica* B lipase from Novo Nordisk). After the reaction mixture had been stirred for 6 hours at 80° C./1013 mbar, the pressure was slowly reduced to 200 mbar to continuously distill off the ethanol. The reaction time was 3 hours. The immobilized enzyme was then removed by filtration. A clear viscous liquid with a molecular weight (as determined from GPC data and calibration with polystyrene) of ca. 1500 and an acid value of ca. 93 was obtained in a yield of about 400 g. The product is soluble in water.

Example 5

46.1 g (1 mole) of ethanol and 92.1 g (1 mole) of glycerol were added to 150.1 g (1 mole) of L-(+)-tartaric acid and the reaction was started with 12.1 g (5% by weight) of Novozymrn 435 (immobilized *Candida antarctica* B lipase from Novo Nordisk). After the reaction mixture had been stirred for 5 hours at 80° C./1013 mbar, the pressure was reduced in 24 hours to 200 mbar and, after another 24 hours, to 50 mbar to continuously distill off the ethanol. The immobilized enzyme was then removed by filtration. A viscous liquid with a molecular weight (as determined from GPC data and calibration with polystyrene) of ca. 1100 and an acid value of ca. 122 was obtained in a yield of about 200 g.

What is claimed is:

1. A process for preparing linear polyesters, said process comprising:
    (a) providing a reaction mixture comprising a dicarboxylic acid having from 2 to 10 carbon atoms, a polyol having from 2 to 15 carbon atoms, a low-boiling primary alcohol and a catalytic-effective amount of a lipase, wherein the reaction mixture is free of additional solvents; and
    (b) reacting the dicarboxylic acid and the polyol.
2. The process according to claim 1, wherein the dicarboxylic acid comprises a hydroxydicarboxylic acid having two or more primary hydroxyl groups.
3. The process according to claim 1, wherein the dicarboxylic acid comprises tartaric acid.
4. The process according to claim 1, wherein the dicarboxylic acid comprises a mixture of two or more dicarboxylic acids.
5. The process according to claim 4, wherein the dicarboxylic acid comprises a hydroxydicarboxylic acid having two or more primary hydroxyl groups.
6. The process according to claim 4, wherein the dicarboxylic acid comprises tartaric acid.
7. The process according to claim 1, wherein the polyol comprises a component selected from the group consisting of glycerol, alkylene glycols, technical oligoglycerol mixtures, methylol compounds, lower alkyl glucosides, sugar alcohols, sugars, amino sugars, and mixtures thereof.
8. The process according to claim 7, wherein the dicarboxylic acid comprises a hydroxydicarboxylic acid having two or more primary hydroxyl groups.
9. The process according to claim 7, wherein the dicarboxylic acid comprises tartaric acid.
10. The process according to claim 7, wherein the dicarboxylic acid comprises a mixture of two or more dicarboxylic acids.
11. The process according to claim 10, wherein the dicarboxylic acid comprises a hydroxydicarboxylic acid having two or more primary hydroxyl groups.
12. The process according to claim 1, wherein the lipase comprises a component selected from the group consisting of *Candida antartica* B and *Rhizomucor miehei*.
13. The process according to claim 1, wherein the dicarboxylic acid and the polyol are reacted in a molar ratio of from 2:1 to 0.5:1.
14. The process according to claim 1, wherein the dicarboxylic acid and the polyol are reacted in a molar ratio of from 1.2:1 to 0.8:1.
15. The process according to claim 1, wherein the low-boiling primary alcohol is present in a molar amount of from 0.1 to 5, based on the molar amount of the dicarboxylic acid.
16. The process according to claim 1, wherein the reaction of the dicarboxylic acid and the polyol is carried out at a pressure of from 0.01 to 500 mbar.

17. The process according to claim 1, wherein the reaction of the dicarboxylic acid and the polyol is carried out at a pressure of from 10 to 250 mbar.

18. A process for preparing linear polyesters, said process comprising:
(a) providing a reaction mixture comprising; a dicarboxylic acid component comprising a mixture of a hydroxydicarboxylic acid having two or more primary hydroxyl groups and an additional dicarboxylic acid; a polyol component selected from the group consisting of glycerol, alkylene glycols, technical oligoglycerol mixtures, methylol compounds, lower alkyl glucosides, sugar alcohols, sugars, amino sugars, and mixtures thereof, a low-boiling primary alcohol; and a catalytic-effective amount of a lipase selected from the group consisting of *Candida antartica* B and *Rhizomucor miehei*, wherein the reaction mixture is free of additional solvents; and
(b) reacting the dicarboxylic acid and the polyol in a molar ratio of from 1.2:1 to 0.8:1, and at a pressure of from 10 to 250 mbar.

* * * * *